(12) United States Patent
Calasso et al.

(10) Patent No.: US 12,318,574 B2
(45) Date of Patent: Jun. 3, 2025

(54) DEVICE AND SYSTEM FOR DELIVERING A MEDICAL FLUID AND RELATIVE DELIVERY METHOD

(71) Applicant: Stevanato Group S.p.A., Piombino Dese (IT)

(72) Inventors: Irio Giuseppe Calasso, Visp (CH); Matteo De Donatis, Visp (CH)

(73) Assignee: Stevanato Group S.p.A., Piombino Dese (IT)

( * ) Notice: Subject to any disclaimer, the term of this patent is extended or adjusted under 35 U.S.C. 154(b) by 1044 days.

(21) Appl. No.: 17/296,278

(22) PCT Filed: Dec. 17, 2019

(86) PCT No.: PCT/IB2019/060906
§ 371 (c)(1),
(2) Date: May 24, 2021

(87) PCT Pub. No.: WO2020/128821
PCT Pub. Date: Jun. 25, 2020

(65) Prior Publication Data
US 2022/0016339 A1    Jan. 20, 2022

(30) Foreign Application Priority Data

Dec. 20, 2018 (IT) .......................... 102018000020467

(51) Int. Cl.
*A61M 5/168* (2006.01)
*A61M 5/145* (2006.01)
(Continued)

(52) U.S. Cl.
CPC .......... *A61M 5/168* (2013.01); *A61M 5/1452* (2013.01); *A61M 5/158* (2013.01);
(Continued)

(58) Field of Classification Search
CPC ........... A61M 2205/8287; A61M 2005/14208; A61M 2005/14252; A61M 5/158
See application file for complete search history.

(56) References Cited

U.S. PATENT DOCUMENTS 8,632,507 B2    1/2014  Bartha
10,493,201 B2  12/2019  Cole et al.
(Continued)

FOREIGN PATENT DOCUMENTS

CN    101951979 A    1/2011
CN    106999671 A    8/2017
(Continued)

*Primary Examiner* — Nathan R Price
*Assistant Examiner* — Haden Matthew Ritchie
(74) *Attorney, Agent, or Firm* — Blank Rome LLP

(57) ABSTRACT

A device for delivering a medical fluid (4) comprising a body which houses: at least one containment tank (20) of a medical fluid, a fluid injection device (24) which interfaces with said containment tank (20) and is suitable to allow controlled delivery of a fluid through a cannula (32), an extraction device (40) of the cannula (32) from a retracted or rest configuration to an extracted or infusion configuration, activation means (44) which comprise a rotor (48), rotatable about a rotation axis (X-X) in an injection rotation direction (I) and in a control rotation direction (C), opposite each other.

24 Claims, 5 Drawing Sheets

(51) Int. Cl.
*A61M 5/158* (2006.01)
*A61M 5/14* (2006.01)
*A61M 5/142* (2006.01)

(52) U.S. Cl.
CPC ............... *A61M 2005/1402* (2013.01); *A61M 2005/14208* (2013.01); *A61M 2005/14252* (2013.01); *A61M 2205/103* (2013.01); *A61M 2205/8287* (2013.01)

(56) References Cited

U.S. PATENT DOCUMENTS

| | | |
|---|---|---|
| 10,576,212 B2 | 3/2020 | Marsh et al. |
| 10,625,018 B2 | 4/2020 | Destafano et al. |
| 11,167,082 B2 | 11/2021 | Laurence et al. |
| 2008/0269687 A1 | 10/2008 | Chong et al. |
| 2009/0105650 A1 | 4/2009 | Wiegel et al. |
| 2012/0245515 A1* | 9/2012 | Calasso ............... A61M 5/1413 604/67 |
| 2016/0089491 A1 | 3/2016 | Smith |
| 2017/0021096 A1* | 1/2017 | Cole ................. A61M 5/14248 |

FOREIGN PATENT DOCUMENTS

| | | |
|---|---|---|
| CN | 206642180 U | 11/2017 |
| CN | 107847664 A | 3/2018 |
| EP | 3260151 A1 * | 12/2017 |
| EP | 2731642 B1 | 9/2018 |
| JP | 2017-513619 A | 6/2017 |
| JP | 2018-507747 A | 3/2018 |
| WO | WO 2015/164647 A1 | 10/2015 |
| WO | WO 2016/130679 A2 | 8/2016 |
| WO | WO 2017/219155 A1 | 12/2017 |

\* cited by examiner

DEVICE AND SYSTEM FOR DELIVERING A MEDICAL FLUID AND RELATIVE DELIVERY METHOD

FIELD OF APPLICATION

The present invention relates to a device and a system for delivering a medical fluid, by transdermal, intramuscular or intravenous route, and to the relative method of delivering a medical fluid by transdermal, intramuscular or intravenous route.

PRIOR ART

Some medical conditions require regular dosing or continuous infusion of medications. These medications are often supplied as liquid solutions to be infused, e.g. by transdermal route. For example, diabetic patients may require insulin. In an attempt to facilitate the lives of these patients, various infusion devices have been developed.

Infusion devices known in the art typically comprise simple injection pen devices or complex pump devices, which use mechanical or electromechanical pumping to supply the medication to a patient through the skin.

Injection pen devices require the patient to re-inject repeatedly, are not discrete and are associated with a feeling of discomfort, fear of injection and pain. Furthermore, they lack any kind of control, feedback and safety features. However, they have the advantage of being inexpensive and relatively simple to use.

Pump devices on the other hand comprise a large number of elements necessary for operation and control, e.g. a processor, electrical components, a battery, buttons or switches located on the housing of the device, visual feedback via text or graphic screen, etc. For this reason, they are expensive, difficult to use and tend to be bulky and uncomfortable for the user. Furthermore, they require scrupulous maintenance and cleaning to ensure correct functionality and safety for their long-term use.

These known devices, whether they are of the pen or pump type, must ensure the administration or infusion of the correct pre-established dose in total safety.

This means that before performing any cannula infusion, the so-called priming or initialization, or the filling of the needle or cannula with medical substance, must be carried out. This operation is fundamental because on the one hand it allows establishing with extreme precision the quantity of medical liquid subsequently infused (which is often well below the quantity of liquid that must previously fill the needle or the cannula itself) and on the other it avoids injecting air bubbles in the patient.

Therefore priming is an essential preventive step for the patient's safety.

Equally important are, in particular for pump-type infusers, the steps of insertion of the cannula by means of a support needle.

The known devices provide a plurality of electric/electronic means which verify the execution of the priming and control the steps of insertion of the cannula or of the needle and infusion of the medical liquid.

These electric/electronic means, if on the one hand ensure the reliability of the transdermal delivery device, on the other hand significantly increase the costs, complications and dimensions.

Moreover, in particular for the injection or infusion devices in continuous contact with the skin for the entire duration of the cartridge containing the medical substance, the device is particularly complex, making the cost of the therapy high.

DISCLOSURE OF THE INVENTION

The need of solving the drawbacks and limitations mentioned with reference to the prior art is therefore felt.

Therefore, the need is felt to provide an intramuscular or intravenous transdermal delivery device for a medical fluid that is at the same time reliable and cost-effective, as well as a device that does not have excessive dimensions.

Such a need is met by a device for delivering a medical fluid according to claim 1.

DESCRIPTION OF THE DRAWINGS

Further features and advantages of the present invention will appear more clearly from the following description of preferred non-limiting embodiments thereof, in which.

Elements or parts of elements in common to the embodiments described below are referred to with the same reference numerals.

DETAILED DESCRIPTION

Figure 1:
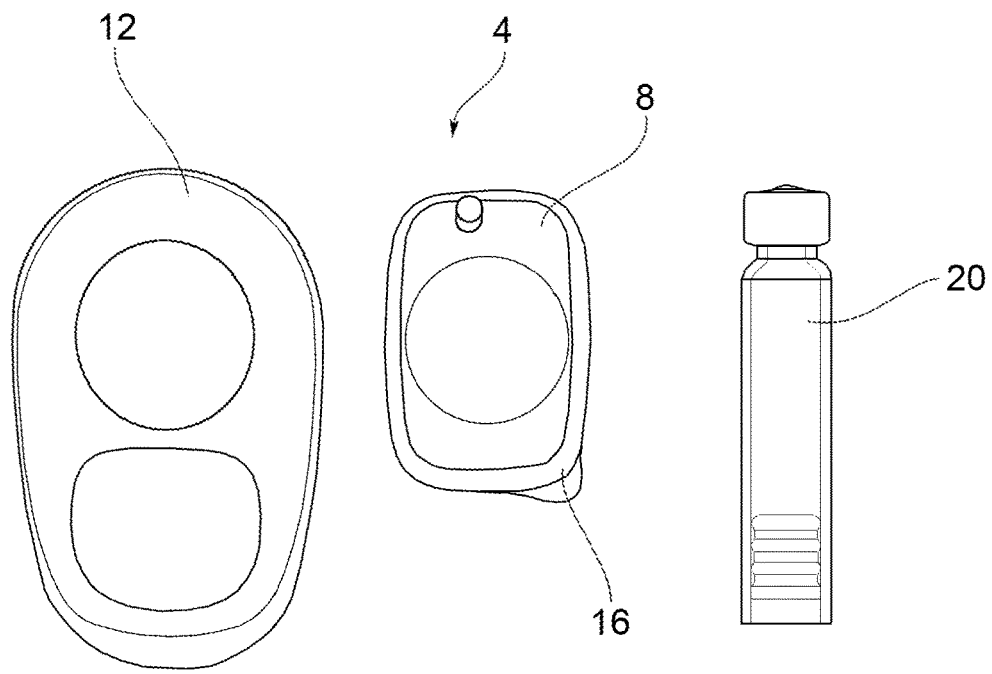
FIG. 1 shows a plan view of a system for delivering a medical fluid comprising a device for delivering a medical fluid, a portable activation device for said device for delivering a medical fluid and a vial of medical fluid, according to a possible embodiment of the present invention.
Figure 2:
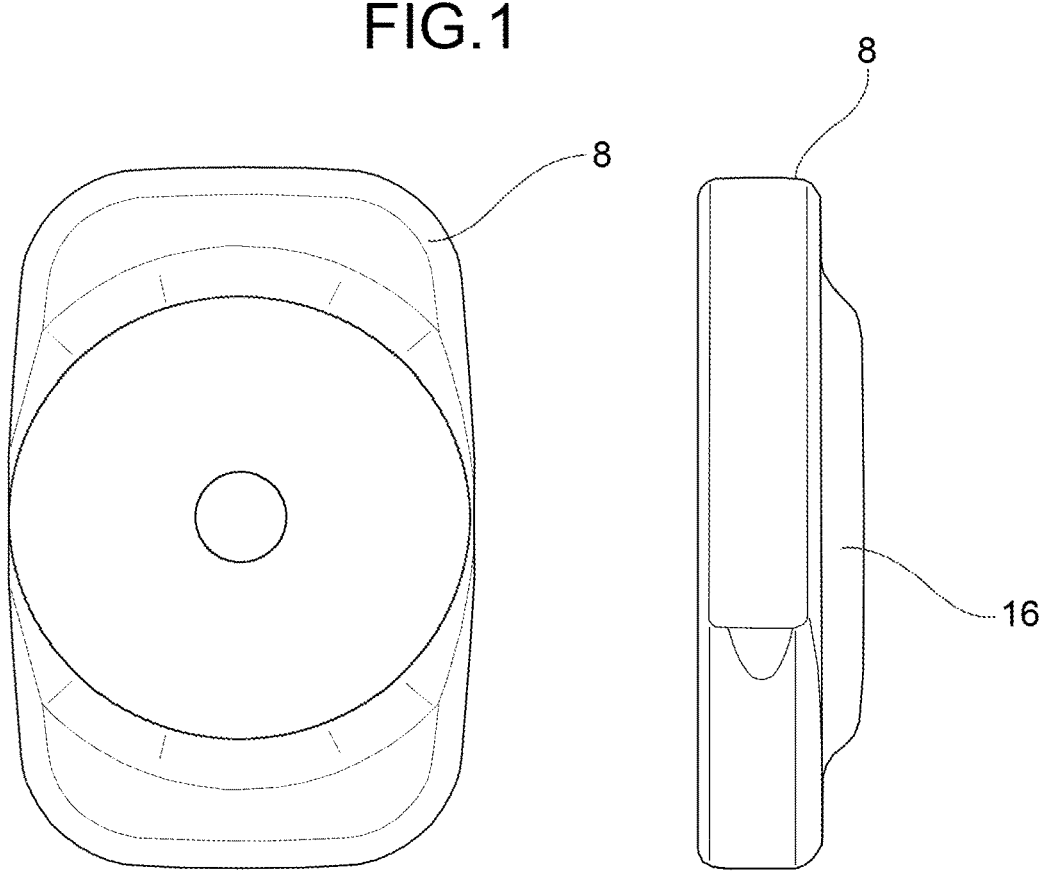
FIG. 2 shows a plan view and a lateral view of a device for delivering a medical fluid according to an embodiment of the present invention.
Figure 4:
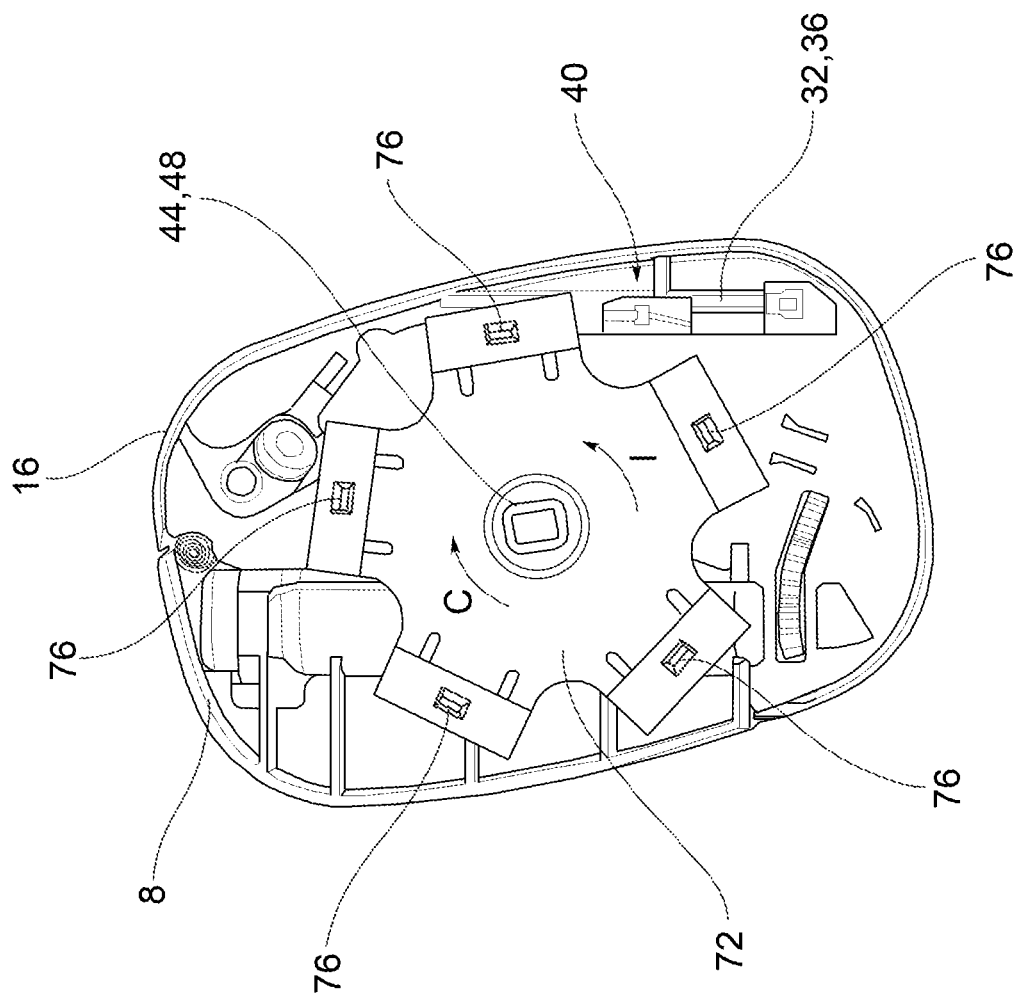
FIG. 4 shows a plan view of the device for delivering a medical fluid of FIG. 3, in which the upper cover has been removed.
Figure 3:
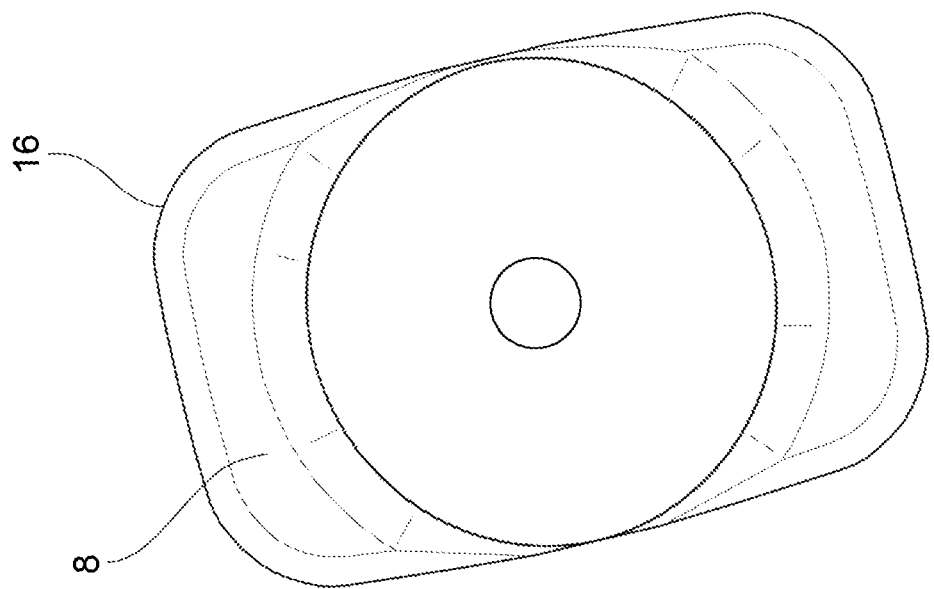
FIG. 3 shows a plan view of a device for delivering a medical fluid according to an embodiment of the present invention in an assembled configuration.
Figure 5:
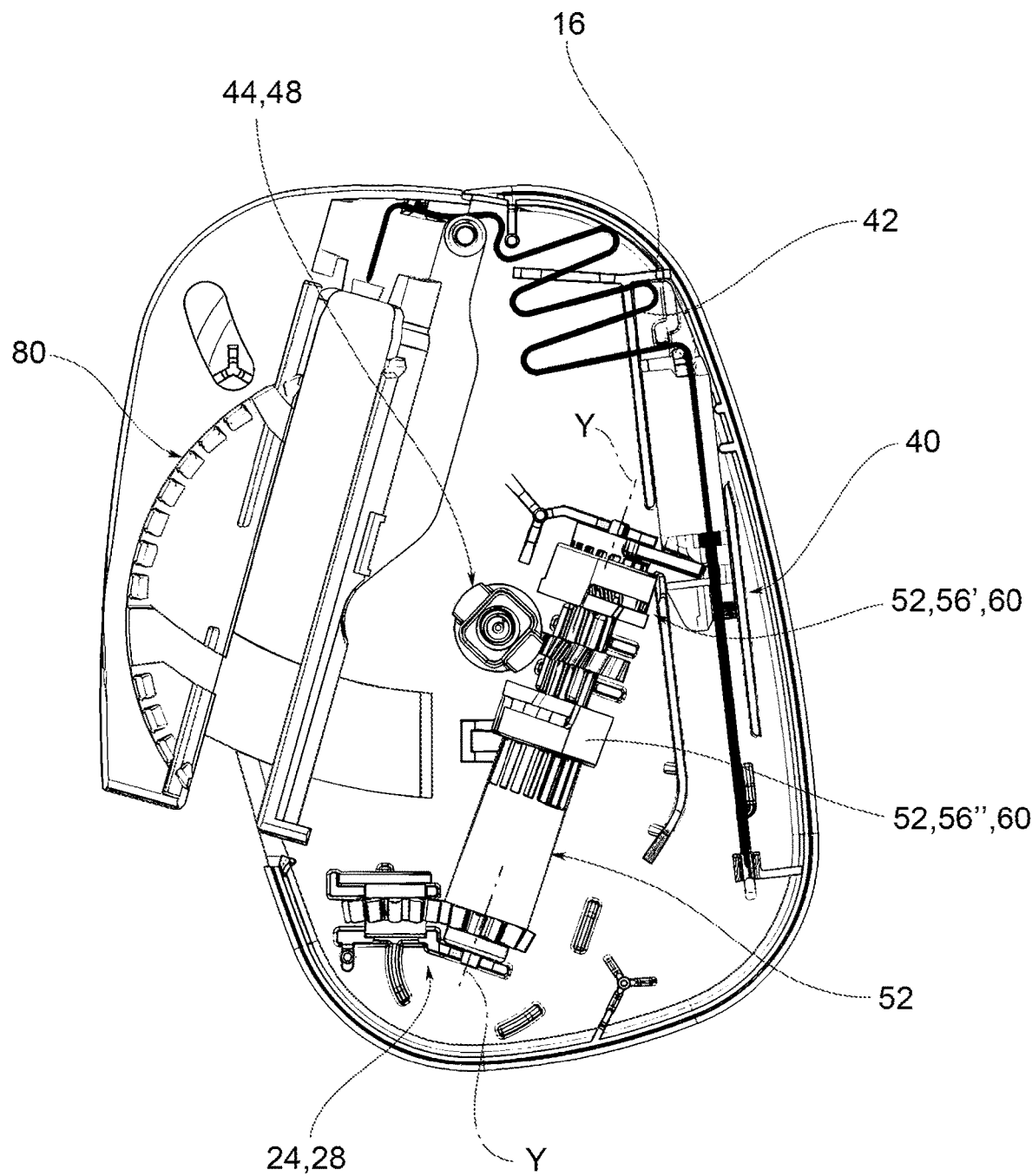
FIG. 5 shows a further plan view of the device for administering medical fluid of FIG. 3, in which the upper cover and other internal components have been removed.
Figure 6:
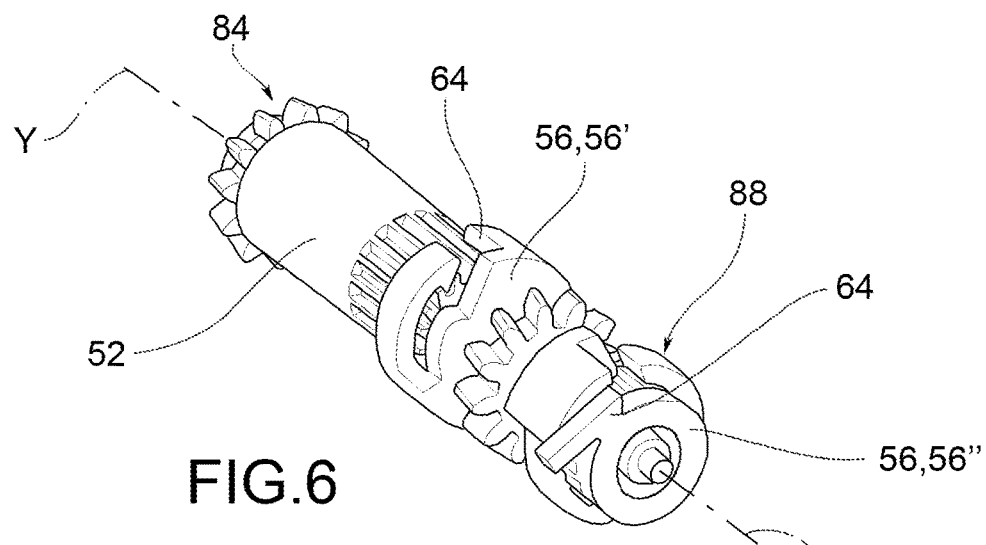
FIG. 6 shows a perspective view of a control shaft of a device for delivering a medical fluid according to a possible embodiment.
Figure 7:
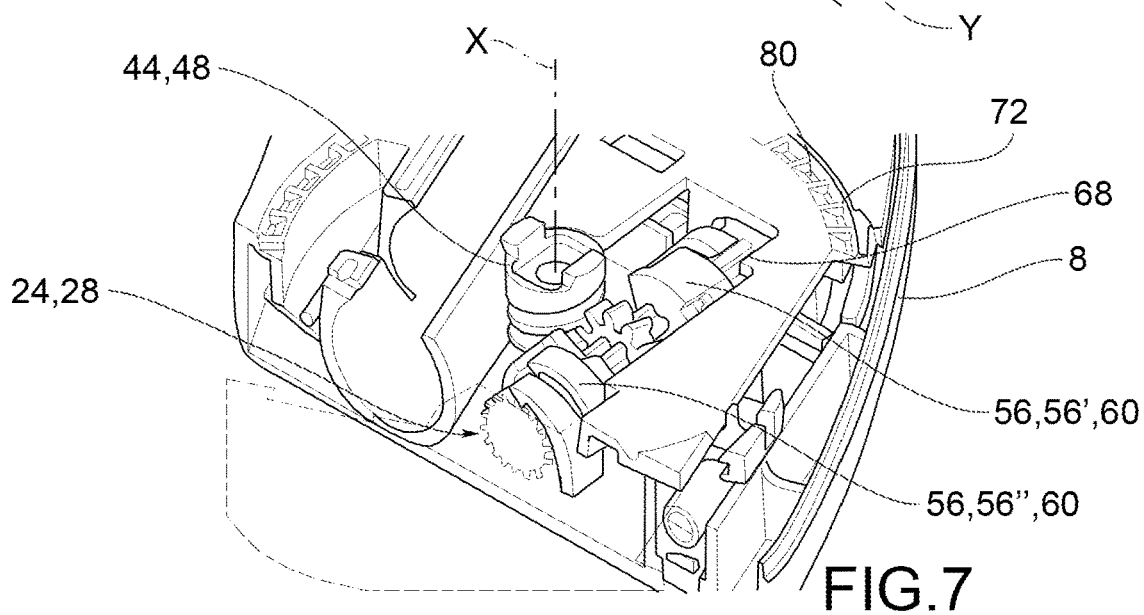
FIGS. 7-9 show partial perspective views of some internal components of a device for delivering a medical fluid according to a possible embodiment of the present invention.
Figure 8:
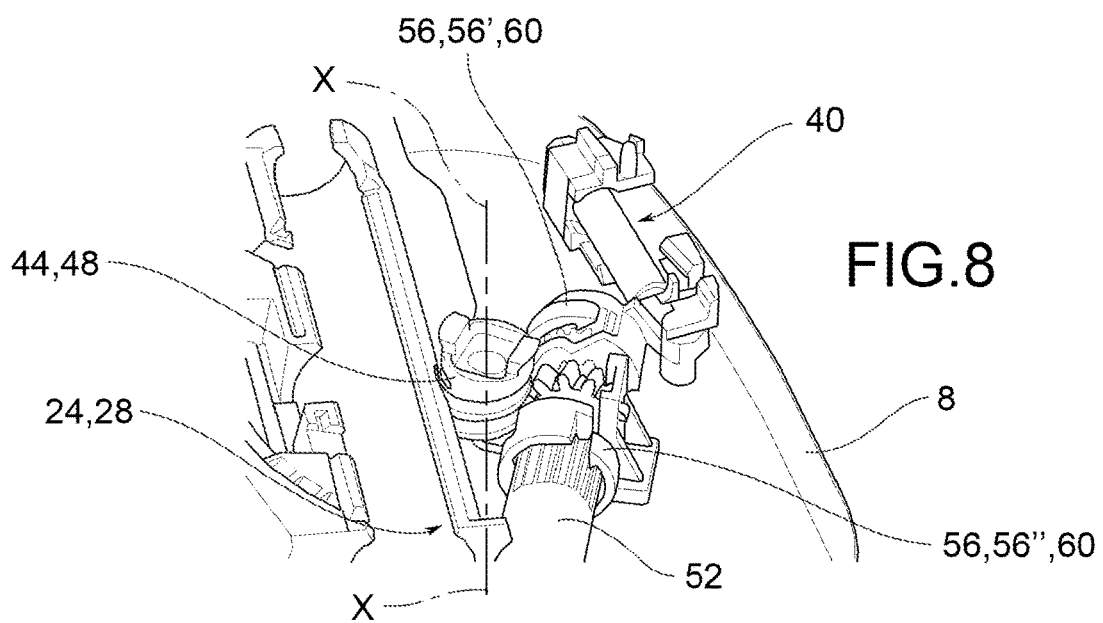
Figure 9:
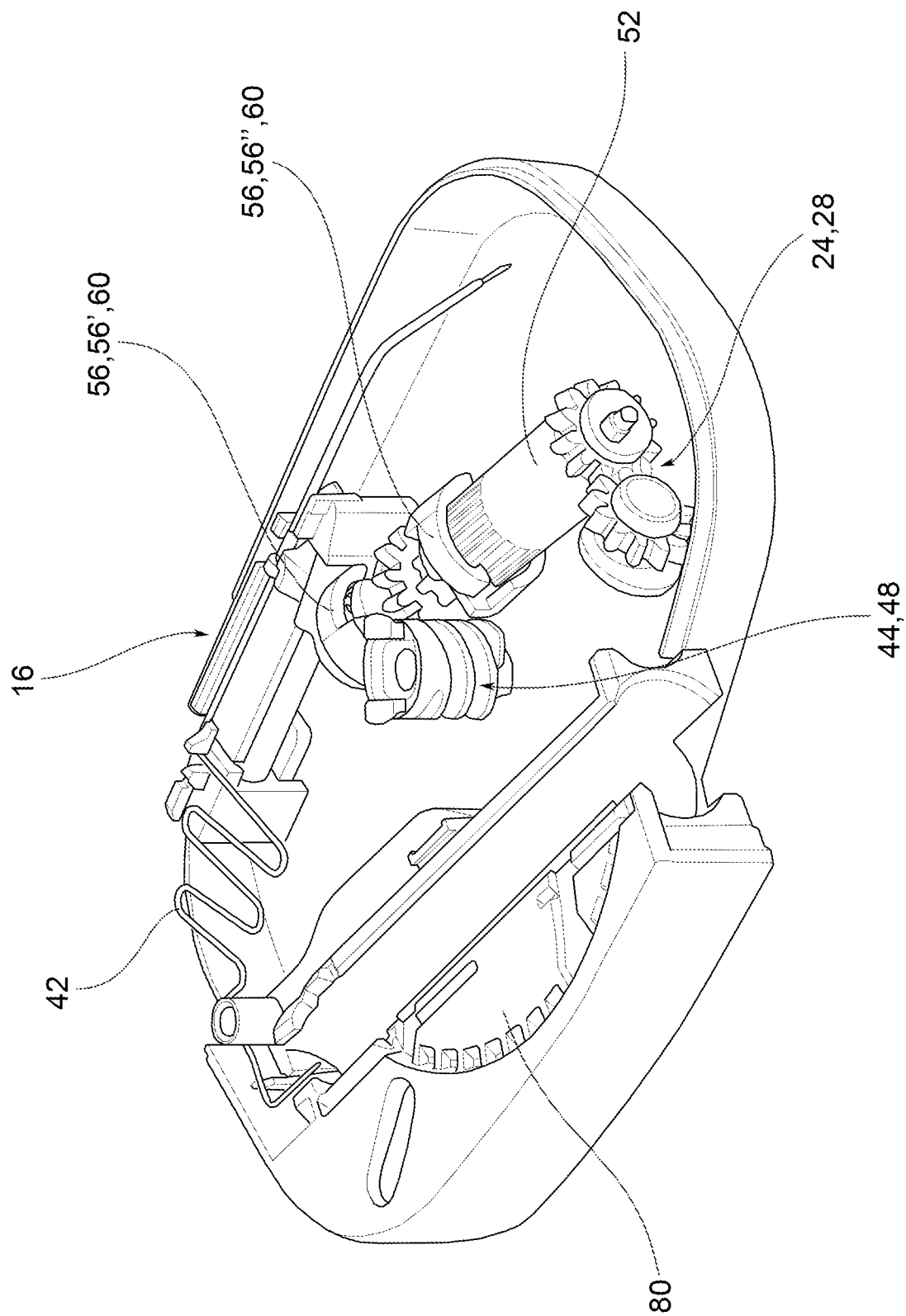

With reference to the aforementioned figures, reference numeral 4 globally indicates an overall view of a system for delivering a medical fluid comprising a device for delivering a medical fluid 8 and a portable activation device 12 of said device for delivering a medical fluid 8.

The device for delivering a medical fluid 8 is a device that is configured to be positioned in contact with a patient and to perform a medical treatment by regulating or infusing a flow of fluid into the patient's body or out of the patient's body. "Regulating or infusing a fluid flow" means changing, e.g. increasing, decreasing, starting, interrupting or resuming the flow of a fluid. This may comprise pumping a fluid continuously or at intervals, with constant or variable flow.

"In contact" means in dermal contact with the patient, e.g. fixed in a removable way, e.g. by an adhesive layer, to the patient's skin, directly or indirectly, e.g. only through an infusion element, such as a catheter or the like, or more generally, it means a body contact, comprising the inside of the body, as in the case of a device fixed at least partly inside or outside the body, e.g. implanted inside the body.

An example of a fluid is a medicament to treat a medical condition, e.g. insulin for the treatment of a diabetic condition, a drug for the treatment of pain for example to treat the symptoms of a chronic disease, an anticoagulant drug to reduce the risk of thrombosis, e.g. after surgery, a hormone to treat or change other medical conditions, etc. The fluid may otherwise be a body fluid or an external fluid that passes through a fluidic conduit of the body.

The device for delivering a medical fluid 8 comprises a body 16 which houses at least one containment tank 20 of a medical fluid, such as for example a vial, a tube, a carpule and the like, both in glass comprising or in plastic material which can be flexible or not. The containment tank 20 can be inserted into the device manually even before use or already housed in the device itself by the manufacturer. The containment tank 20 can contain the medical fluid or be filled with the medical fluid manually.

The body 16 also houses a fluid injection device 24 which interfaces with said containment tank 20 and is suitable to allow controlled delivery outside the tank itself.

According to possible embodiments, the fluid injection device 24 is a medical infusion device configured to deliver multiple transdermal or intramuscular or intravenous doses of a fluidic medicament to a patient. A typical example of a patient is a diabetic patient who requires frequent doses of insulin, e.g. at each meal.

The fluid injection device 24 may be made as a valve device configured to enable/disable the fluid flow or vary the flow rate of a fluid, e.g. a body fluid or as a continuous infusion device, configured to deliver a continuous flow of a medicament with a flow rate which can be modified over time.

According to an embodiment, the fluid injection device 24 is an axial pump element which at the time of translation causes, directly or indirectly, fluid displacement.

According to an embodiment, the axial pump element is a thrust or pulling element such as a plunger or piston 28 or is coupled to a plunger or piston in turn coupled or that can be coupled to said containment tank 20, preferably of the cartridge type. According to this embodiment, the translation of the plunger or piston 28 causes the displacement and therefore the controlled delivery of the medical fluid.

According to other embodiments, the injection device 24 can be an element of a pump or a valve for regulating the flow of a fluid.

A "pump" can be any type of pumping mechanism, e.g. a peristaltic pump, a diaphragm pump, a micropump, as known in the art, and configured to pump a fluid through a fluidic conduit. The pumping of the fluid can take place both in suction and in thrust. A "valve" may be any type of valve having at least one valve inlet and at least one valve outlet for interrupting, resuming, diverting, decreasing or increasing the flow or pressure of a fluid in a fluidic conduit.

The delivery device 8 is also provided with a cannula 32 fluidly connected or connectable to the containment tank 20 for the delivery of said fluid.

According to a possible embodiment, the delivery device 8 can also be provided with a tip 36, shaped to allow the transdermal or intramuscular insertion of said cannula 32.

In other words, the tip 36 is a solid or hollow inside tip, drilled or not drilled, shaped to allow the transdermal or intramuscular insertion of the cannula 32, after the insertion and retraction of the tip 36 itself so that the cannula 32 partly remains in the skin while the tip is retracted.

It should be noted that by cannula 32 it is meant any device, at least partially hollow, able adapted to transport a liquid transdermally or intramuscularly and then inject a medical liquid.

Therefore the cannula 32 can be a tubular element, with or without a tip, or it can also be a needle; this cannula 32, for the purposes of the present invention can be made either of plastic material, or of metal or other biocompatible components suitable for the purpose.

Therefore, for the purposes of the present invention, the presence of a tip inside the cannula 32 is required for the insertion of the cannula 32 into the skin and that the tip retracts so that the cannula remains partly in the skin and therefore the delivery of medical fluid can pass inside the cannula 32.

In other possible configurations, the tip may be optional and not necessary.

The delivery device 8 also comprises an extraction device 40 of the cannula 32 from a retracted or rest configuration to an extracted or infusion configuration. This extraction device 40 can be configured in various ways, all preferably adapted to allow an extraction movement of the cannula and of the tip or simply of the cannula: moreover, said extraction device 40 is configured to synchronize the movement of the tip 36 (if provided) with the movement of the cannula 32, since after the tip 36 has been extracted and penetrated into the skin, the same needle must retract while part of the cannula 32 remains inserted in the skin, so that the cannula 32 is ready to inject the medical substance.

The extraction of the tip 36 and/or of the cannula 32 takes place preferably by means of elastic means 42, such as for example a suitably shaped and folded spring.

The device for delivering a medical fluid 8 further comprises activation means 44 which comprise a rotor 48, rotatable about a rotation axis X-X in an injection rotation direction I and in a control rotation direction C, to check whether the extraction of the cannula took place, opposite each other.

The extraction of the cannula 32 can be activated either in the fluid injection rotation direction or alternatively in the control rotation direction C.

According to an embodiment, the rotor 48 is mechanically engaged with a control member 52 operatively connected to said fluid injection device 24 and to said extraction device 40 of the cannula 32. In this way, a single control member 52, after relative rotation, is able to activate or enable the operation both of the fluid injection device 24 and of the extraction device 40 of the cannula 32 which controls if the cannula 32 has been extracted.

According to a possible embodiment, said control member 52 is made with separate control shafts which are enabled to rotate at least in part in opposite directions.

According to a possible embodiment, said control member 52 is a control shaft.

In particular, each of said fluid injection 24 and extraction 40 devices is operatively connected to the control shaft 52 by means of a one-way transmission mechanism 56', 56" which allows the transmission of motion in a direction of rotation and at least partly prevents it in the opposite direction.

In particular, said one-way transmission mechanisms 56', 56" allow the transmission of motion in one of said rotation directions of the control shaft 52 and prevent it at least in part in the other direction of rotation.

Said one-way transmission mechanisms 56', 56" are opposed to each other so that the rotation of the control shaft 40 in the control rotation direction C allows checking the state of the extraction device 40 of the cannula 32 and the rotation of the control shaft 40 in the injection rotation direction I allows the activation of the fluid injection device 24.

The one-way transmission mechanism 56 can be of various types; according to a possible embodiment, said one-way transmission mechanism 56 is a freewheel mechanism.

According to an embodiment, said one-way transmission mechanism 56 comprises an asymmetric cam 60, shaped so as to transmit the motion of a direction of rotation, by interference with a corresponding abutment 64, and to prevent the transmission of motion in an opposite direction of rotation.

According to a further embodiment, said one-way transmission mechanism 56 comprises a clutch mechanism, shaped so as to transmit motion in a direction of rotation by friction, and to prevent transmission of motion in an opposite direction of rotation.

It should be noted that the one-way transmission mechanisms 56', 56" with which the control shaft 52 is provided are not necessarily the same as each other; for example they can be of the friction type and of the freewheel type, mounted simultaneously on the same control shaft 52. The important thing is not the type of the one-way transmission mechanism, but the fact that the two mechanisms 56', 56" are mounted mutually reversed so that by rotating the control shaft 52 in any direction, one of the two one-way transmission mechanisms 56' is active and allows the transmission of the motion or a motion enabling to the relative injection/extraction and control or injection and extraction/control device connected to it, while the other one-way transmission mechanism 56" at least partially prevents it.

Preferably, the body 16 comprises an extraction end stop 68 which causes a stop for the extraction device 40 of the cannula 32 after having carried out or activated the extraction of the cannula 32 itself.

As mentioned above, the control shaft 52 takes the rotary motion from the rotor 48, rotatable about a rotation axis X-X in an injection rotation direction I and in a control rotation direction C, opposite each other.

For example, the rotor 48 is mechanically engaged with the control shaft 52 by means of a toothed coupling, preferably of an irreversible type.

Preferably, the rotor 48 is rotatable about a rotation axis X-X which is perpendicular to a control axis Y-Y around which the control shaft 52 rotates.

In turn, the rotor 48 is mechanically connected to a disc 72, for example provided with magnetic or ferromagnetic activation elements 76.

Said disc 72 is preferably provided with holes 80 mutually angularly arranged to prevent uncontrolled rotation of the rotor 48.

The control shaft 52, as seen, is interposed between the extraction device 40 of the cannula 32 and the fluid injection device 24.

Preferably, the control shaft 52 is connected to the extraction device 40 of the cannula 32 and to the fluid injection device 24 at its opposite axial ends 84, 88.

The rotor 48 is preferably arranged at a center of the body 16.

As mentioned above, the present invention also relates to a system for delivering a medical fluid 4 comprising the device for delivering a medical fluid 8 and a portable activation device 12 for said delivery device 8.

In detail, the activation device 12 is a portable device provided with a control unit for magnetically rotating the rotor 48 or for transferring electromagnetic or magnetic energy to activate or transfer energy for the operation of the delivery device 8 and to detect, via a relative sensor, the actual rotation of the rotor 48.

The activation device 12 (also called handheld) is portable and is gripped by the user when he/she wants to make an injection of medical liquid.

According to an embodiment, the activation of the delivery device 8 takes place by magnetic rotation of the disc 72 provided with the magnets or ferromagnetic activation elements 76; in turn the disc 72 transmits torque to the rotor 48 which rotates the control shaft 52 in a predetermined direction, based on the action requested by the user.

According to an embodiment, the activation of the delivery device 8 takes place by means of energy transfer, through magnetic coupling or electromagnetic induction transfer which feeds a motor and/or an electrical circuit so as to rotate the control shaft 52 in a predetermined direction, based on the action requested by the user.

According to an embodiment, said control unit is provided with a controller that, in the case of an injection request of a fluid or initialization, is programmed to:
control the rotation of the control shaft 52 in the control rotation direction C, to check if the cannula 32 has been completely extracted,
in case of negative verification, i.e. in case of non-extraction of the cannula 32, invert the rotation of the control shaft 52 in the direction of injection rotation I, and make a first initialization injection of the cannula 32 (priming) to fill said cannula 32 with fluid.

Furthermore, the control unit is programmed to, following the first initialization injection:
control or enable the extraction of the cannula 32 by said extraction device 40,
inject the medical fluid by controlling the rotation of the control shaft 52 in the injection rotation direction I.

Furthermore, in the event of a fluid injection request, the control unit is programmed to:
control the rotation of the control shaft 52 in the control rotation direction C, to check if the cannula has been completely extracted,
in case of positive verification, invert the rotation of the control shaft 52 in the injection rotation direction I, and inject the fluid according to a predetermined dose.

The verification is positive if the rotation of the control shaft 52 in the injection rotation direction I is prevented due to the fact that the stroke end of the one-way transmission device 56 for the extraction of the cannula 32 has already previously been reached.

Furthermore, in the event of an initialization request, the control unit is programmed to:
check in advance that the cannula 32 has been extracted, by controlling the rotation of the control shaft 52 in the control rotation direction C,
in case of negative verification, i.e. of non-extraction of the cannula 32, perform said initialization by rotation of the control shaft 52 in the injection rotation direction I,
in case of positive verification, i.e. of verification of extraction of the cannula 32, not to perform said initialization step.

The verification is negative if, following the command to rotate the control shaft 52 in the control rotation direction C, this rotation is not prevented: this in fact implies that there is still a useful stroke of the one-way transmission device 56 and therefore, the cannula 32 is not extracted.

Furthermore, following the initialization step, the control unit is programmed so as to be able to perform the subsequent injections of medical fluid which can be different doses based on the patient's need.

According to a possible embodiment, the actuation of the extraction device 40 of the cannula 32 is carried out simultaneously with the next first rotation of the control shaft 52 in the injection rotation direction I.

The operation and therefore the method of delivering a fluid by means of a delivery device according to the invention will now be described.

In particular, the method of delivering a medical fluid according to the present invention, in the case of a fluid injection request, can comprise the steps of:

checking if the cannula 32 has been extracted by rotation of the control shaft 52 in the control rotation direction C, in the case of negative verification, i.e. in case of non-extraction, inverting the rotation of the control shaft 52 in the injection rotation direction I, and making a first initialization injection of the cannula 32 (priming) to move the piston up to the plunger of the container and fill said cannula 32 with fluid, and then perform the step of extraction of the cannula 32 by rotating in the control direction to then perform the injection step of a predetermined dose by rotating the control shaft 52 again according to the injection rotation direction I.

In case of positive verification, the step of inverting the rotation of the control shaft 52 in the injection rotation direction I, and injecting the fluid according to a predetermined dose is performed.

Moreover, in the case of an initialization request, the method according to the present invention comprises the steps of:

checking in advance that the cannula 32 has been extracted, by controlling the rotation of the control shaft 52 in the control rotation direction, in case of negative verification, performing said initialization by rotation of the control shaft 52 in the injection rotation direction I, in case of positive verification, not performing said initialization step.

Moreover, the delivery method of the present invention, following the initialization step, provides the step of operating the extraction device 40 of the cannula 32, so as to be able to carry out the subsequent injections of medical fluid.

According to a possible embodiment variant, the actuation of the extraction device 40 of the cannula 32 is carried out simultaneously with the next first rotation of the control shaft 52 in the injection rotation direction I.

It should be noted that the system is always able to establish how much dose to inject both in the initialization step and in the actual injection step as a function of the transmission ratio given by the kinematic chain that connects the control shaft 52 with the injection device 40, and in particular, with the piston 28. In other words, each complete revolution of the control shaft 52 corresponds to a specific stroke of the piston 28 and therefore a volume of injected liquid. For example, with a predefined setting which considers the distance between plunger and piston, the volume of the cannula 32 being known, it is possible to establish how many turns of control shaft/member 52 are needed for a complete initialization. Furthermore, it is possible to determine how many turns or portions of turn the control shaft 52 must perform to inject the exact predetermined dose set by the user.

As can be appreciated from the description, the present invention allows overcoming the drawbacks of the prior art.

In fact, the present invention allows providing an intravenous or transdermal delivery device for a medical fluid that is at the same time reliable and cost-effective, as well as a device that does not have excessive dimensions.

The delivery device exclusively comprises mechanical components and, nevertheless, it allows safety verifications to be made before any medical liquid is infused.

These safety verifications consist of verifying the initialization step (priming) and verifying the complete extraction of the cannula, or its insertion in the patient.

The delivery device is therefore light, compact and cost-effective.

At the same time, this device is extremely reliable.

In fact, the freewheel mechanisms allow the device to discriminate control and injection operations. In particular, any rotation of the control member can generate only one step at a time, be it the extraction step of the cannula or the liquid injection step, or to verify whether the extraction of the cannula has been activated or in certain embodiments if the cannula is extracted.

Therefore the control unit can reliably control the opposite rotations of the control shaft.

The provision of the extraction end stop of the cannula provides a signal to the control unit on the extraction of the cannula and therefore on the possibility of being able to carry out the delivery of the dose and not to carry out the initialization with priming.

A man skilled in the art may make several changes and adjustments to the systems and devices described above in order to meet specific and incidental needs, all falling within the scope of protection defined in the following claims.

The invention claimed is:

1. A device for delivering a medical fluid, the device comprising a body housing:
   at least one containment tank of a medical fluid;
   a fluid injection device which interfaces with the containment tank and is suitable to allow controlled delivery of a fluid through a cannula;
   an extraction device of the cannula movable from a retracted or rest configuration to an extracted or infusion configuration; and
   an activator rotatable about a rotation axis in an injection rotation direction and in a control rotation direction, opposite each other, wherein:
the activator comprises a control shaft configured so that the extraction of the cannula takes place by rotating the control shaft in the injection rotation direction or in the control rotation direction,
the control shaft is operatively connected to a rotor, to the fluid injection device, and to the extraction device of the cannula,
the control shaft is shaped so that, during rotation in the injection rotation direction, the control shaft enables the extraction device of the cannula to extract the cannula if the cannula is in a retracted configuration, and
each of the fluid injection and extraction devices is operatively connected to the control shaft by a one-way transmission mechanism, which allows the transmission of motion in one of said rotation directions of the control shaft and prevents transmission of motion in the other direction of rotation, said one-way transmission mechanisms being opposite each other, so that the rotation of the control shaft in the control rotation direction allows the verification of the status of the extraction device of the cannula and the rotation of the control shaft in the injection rotation direction allows the activation of the fluid injection device.

2. The device for delivering the medical fluid of claim 1, wherein the one-way transmission mechanism is a freewheel mechanism.

3. The device for delivering the medical fluid of claim 1, wherein the one-way transmission mechanism comprises an asymmetric cam, shaped so as to transmit the motion of a direction of rotation, by interference with a corresponding abutment, and to prevent the transmission of motion in an opposite direction of rotation.

4. The device for delivering the medical fluid of claim 2, wherein the freewheel mechanism comprises a clutch mechanism, shaped so as to transmit motion in a direction of rotation by friction, and to prevent transmission of motion in an opposite direction of rotation.

5. The device for delivering the medical fluid of claim 1, wherein the body comprises an extraction end stop determining a stop for the extraction device of the cannula upon reaching the complete extraction of the cannula.

6. The device for delivering the medical fluid of claim 1, wherein the control shaft is shaped so that, during rotation in the control rotation direction, the control shaft verifies the state of the extraction device of the cannula.

7. The device for delivering the medical fluid of claim 1, wherein the fluid injection device is connected to a piston at least partially inserted in the containment tank to provoke the injection of the medical fluid.

8. The device for delivering the medical fluid of claim 1, wherein the rotor is mechanically connected to a disc provided with magnets or ferromagnetic activation elements.

9. The device for delivering the medical fluid of claim 8, wherein the disc is provided with a locking system that prevents rotation of the activator.

10. The device for delivering the medical fluid of claim 1, wherein the control shaft is configured to operate the extraction device of the cannula and the fluid injection device.

11. The device for delivering the medical fluid of claim 1, wherein the control shaft is connected to the extraction device of the cannula and to the fluid injection device at its opposite axial ends.

12. The device for delivering the medical fluid of claim 1, wherein the rotor is arranged at a center of the body.

13. The device for delivering the medical fluid of claim 1, wherein the rotor is driven by a motor.

14. The device for delivering the medical fluid of claim 1, wherein the rotor is mechanically engaged with the control shaft by an irreversible type toothed coupling.

15. A system for delivering a medical fluid, the system comprising:
   an administration device for delivering the medical fluid
     the administration device comprising a body housing:
     at least one containment tank of a medical fluid;
     a fluid injection device which interfaces with the containment tank and is suitable to allow controlled delivery of a fluid through a cannula;
     an extraction device of the cannula movable from a retracted or rest configuration to an extracted or infusion configuration;
     an activator rotatable about a rotation axis in an injection rotation direction and in a control rotation direction, opposite each other, wherein:
     the activator comprises a control shaft configured so that the extraction of the cannula takes place by rotating the control shaft in the injection rotation direction or in the control rotation direction,
     the control shaft is operatively connected to a rotor, to the fluid injection device, and to the extraction device of the cannula, and
     each of the fluid injection and extraction devices is operatively connected to the control shaft by a one-way transmission mechanism, which allows the transmission of motion in one of said rotation directions of the control shaft and prevents transmission of motion in the other direction of rotation, said one-way transmission mechanisms being opposite each other, so that the rotation of the control shaft in the control rotation direction allows the verification of the status of the extraction device of the cannula and the rotation of the control shaft in the injection rotation direction allows the activation of the fluid injection device; and
   a portable activation device of the administration device, the portable activation device comprising:
   a control unit for rotating the rotor of the administration device magnetically or by electromagnetic induction, the control unit comprising a controller that, in case of an injection request of the medical fluid, is programmed to:
     control the rotation of the control shaft in the control rotation direction, to check if the cannula has been completely extracted, and
     in case of negative verification indicating non-complete extraction, invert the rotation of the control shaft in the direction of injection rotation, and make a first initialization injection of the cannula to fill the cannula with the medical fluid; and
   a relative sensor for detecting the effective rotation of the rotor.

16. The system for delivering the medical fluid of claim 15, wherein the controller is programmed, following the first initialization injection, to:
   control or enable the extraction of the cannula by the extraction device, and
   inject the medical fluid by controlling the rotation of the control shaft in the injection rotation direction.

17. The system for delivering the medical fluid of claim 15, wherein the controller, in the case of the injection request of the medical fluid, is programmed to:
   in case of positive verification indicating complete extraction, invert the rotation of the control shaft in the injection rotation direction, and inject the medical fluid according to a predetermined dose.

18. The system for delivering the medical fluid of claim 15, wherein the controller, in the event of an initialization request, is programmed to:
   check in advance that the cannula has been completely extracted by controlling the rotation of the control shaft in the control rotation direction,
   in case of verification of non-extraction of the cannula, perform the initialization by rotation of the control shaft in the injection rotation direction,
   in case of verification of extraction of the cannula, not to perform the initialization step.

19. The system for delivering the medical fluid of claim 18 wherein, following the initialization step, the controller is programmed to operate the extraction device of the cannula so as to be able to perform subsequent injections of the medical fluid.

20. The system for delivering the medical fluid of claim 19, wherein the operation of the extraction device of the cannula is carried out simultaneously with the next first rotation of the control shaft in the injection rotation direction.

21. A method of delivering a medical fluid using an administration device for delivering the medical fluid, the administration device comprising a body housing:
    at least one containment tank of a medical fluid;
    a fluid injection device which interfaces with the containment tank and is suitable to allow controlled delivery of a fluid through a cannula;
    an extraction device of the cannula movable from a retracted or rest configuration to an extracted or infusion configuration; and
    an activator rotatable about a rotation axis in an injection rotation direction and in a control rotation direction, opposite each other, wherein:
the activator comprises a control shaft configured so that the extraction of the cannula takes place by rotating the control shaft in the injection rotation direction or in the control rotation direction,
the control shaft is operatively connected to a rotor, to the fluid injection device, and to the extraction device of the cannula, and
each of the fluid injection and extraction devices is operatively connected to the control shaft by a one-way transmission mechanism, which allows the transmission of motion in one of said rotation directions of the control shaft and prevents transmission of motion in the other direction of rotation, said one-way transmission mechanisms being opposite each other, so that the rotation of the control shaft in the control rotation direction allows the verification of the status of the extraction device of the cannula and the rotation of the control shaft in the injection rotation direction allows the activation of the fluid injection device, the method comprising, in the case of an injection request of the medical fluid, the steps of:
    checking if the cannula has been extracted by rotation of the control shaft in the control rotation direction,
    in the case of negative verification indicating non-complete extraction of the cannula, inverting the rotation of the control shaft in the injection rotation direction, and making a first initialization injection of the cannula to fill said cannula with fluid, and then perform the injection phase of a predetermined dose by rotating the control shaft in the injection rotation direction, and
    in case of positive verification indicating complete extraction of the cannula, invert the rotation of the control shaft in the injection rotation direction, and inject the medical fluid according to the predetermined dose.

22. A method of delivering a medical fluid using an administration device for delivering the medical fluid, the administration device comprising a body housing:
    at least one containment tank of a medical fluid;
    a fluid injection device which interfaces with the containment tank and is suitable to allow controlled delivery of a fluid through a cannula;
    an extraction device of the cannula movable from a retracted or rest configuration to an extracted or infusion configuration; and
    an activator rotatable about a rotation axis in an injection rotation direction and in a control rotation direction, opposite each other, wherein:
the activator comprises a control shaft configured so that the extraction of the cannula takes place by rotating the control shaft in the injection rotation direction or in the control rotation direction,
the control shaft is operatively connected to a rotor, to the fluid injection device, and to the extraction device of the cannula, and
each of the fluid injection and extraction devices is operatively connected to the control shaft by a one-way transmission mechanism, which allows the transmission of motion in one of said rotation directions of the control shaft and prevents transmission of motion in the other direction of rotation, said one-way transmission mechanisms being opposite each other, so that the rotation of the control shaft in the control rotation direction allows the verification of the status of the extraction device of the cannula and the rotation of the control shaft in the injection rotation direction allows the activation of the fluid injection device,
the method comprising, in the case of an initialization request, the steps of:
    checking in advance that the cannula has been extracted, by controlling the rotation of the control shaft in the control rotation direction,
    in case of negative verification indicating non-complete extraction of the cannula, performing the initialization step by rotation of the control shaft in the injection rotation direction, and
    in case of positive verification indicating complete extraction of the cannula, not performing the initialization step.

23. The method of delivering the medical fluid of claim 22 wherein, following the initialization step, the step of operating the extraction device of the cannula is envisaged, so as to be able to carry out subsequent injections of the medical fluid.

24. The method of delivering the medical fluid of claim 23, wherein the operation of the extraction device of the cannula is carried out simultaneously with the next first rotation of the control shaft in the injection rotation direction.

* * * * *